United States Patent [19]

Hall

[11] Patent Number: 5,242,759
[45] Date of Patent: Sep. 7, 1993

[54] JOINT, A LAMINATE, AND A METHOD OF PREPARING A NICKEL-TITANIUM ALLOY MEMBER SURFACE FOR BONDING TO ANOTHER LAYER OF METAL

[75] Inventor: Todd A. Hall, Bloomington, Ind.

[73] Assignee: Cook Incorporated, Bloomington, Ind.

[21] Appl. No.: 703,493

[22] Filed: May 21, 1991

[51] Int. Cl.⁵ .................. B32B 5/14; B32B 15/00; B23K 35/363
[52] U.S. Cl. .................. 428/610; 428/660; 228/207; 228/262.72; 427/309; 427/310
[58] Field of Search ............... 428/610, 660; 228/207, 228/223, 263.21, 263.13; 427/310, 309

[56] References Cited

U.S. PATENT DOCUMENTS

| | | | |
|---|---|---|---|
| 2,858,600 | 11/1958 | Vigor | 428/660 |
| 2,882,593 | 4/1959 | Merlub-Sobel et al. | 228/223 |
| 2,906,008 | 9/1959 | Boegehold et al. | 428/660 |
| 3,002,265 | 10/1961 | Stalker | 228/207 |
| 3,037,880 | 6/1962 | Hamink | 427/310 |
| 3,923,609 | 12/1975 | Welch et al. | 204/16 |
| 3,956,076 | 5/1976 | Welch et al. | 204/286 |
| 4,024,303 | 5/1977 | Hahn | 428/660 |
| 4,331,258 | 5/1982 | Geschwind | 220/359 |
| 4,427,746 | 1/1984 | Takamura | 428/660 |
| 4,984,581 | 1/1991 | Stice | 128/772 |

FOREIGN PATENT DOCUMENTS

| | | | |
|---|---|---|---|
| 56-81665 | 7/1981 | Japan | 428/660 |
| 58-167073 | 10/1983 | Japan | 228/263.21 |
| 59-116342 | 7/1984 | Japan | 228/263.21 |
| 746648 | 3/1956 | United Kingdom | 228/263.21 |

OTHER PUBLICATIONS

Manko, H. H., "Solders and Soldering", McGraw Hill Book Co., 1964, pp. 8-11, 14-15, 112-113, 174-183.
Buehler, W. J. et al., "Summary of Recent Research on the Nitinol Alloys . . . ", Pergamon Press, Oxford, Ocean Engng. vol. 1, pp. 105-120 (1968).
Buehler, W. J. et al., "55-Nitinol-Unique Alloy Wire", preprint of Wire Journal article, pp. 1-15, no date.
Abstract of Japanese Patent Application Serial No. 90JP-286448, JP 04162982-A, Jun. 8, 1992.
Chan, C. M., et al., "Oxidation of an NiTi Alloy", *Surface and Interface Analysis*, vol. 15, pp. 349-354 (1990).

*Primary Examiner*—John Zimmerman
*Attorney, Agent, or Firm*—Richard J. Godlewski

[57] ABSTRACT

A joint and a laminate including a nickel-titanium alloy such as nitinol and a method for preparing the surface of a nickel-titanium alloy member for bonding solder material and, electively, another similar or dissimilar member thereto. The method includes applying an aluminum paste flux to the titanium oxide coated surface of a nickel-titanium alloy member and heating the flux to its activation temperature. The flux removes and suspends the titanium oxide therein along with leaching titanium from the base alloy member surface to form a nickel-rich interface surface. The activated flux also coats the nickel-rich interface layer for protection from further oxidation. A bonding material such as a tin-silver solder is flowed onto the nickel-rich interface surface to displace the activated flux. Electively, another member is applied to the molten solder to form a joint between the two members. The residual flux is cleaned from the joint to prevent further deterioration of the base metal. The solder joint includes the base nickel-titanium alloy metal, the nickel-rich interface surface, and the solder material. Electively, any other member may be applied to this joint in the molten state to form a metallic bond therebetween.

46 Claims, 4 Drawing Sheets

JOINT, A LAMINATE, AND A METHOD OF PREPARING A NICKEL-TITANIUM ALLOY MEMBER SURFACE FOR BONDING TO ANOTHER LAYER OF METAL

TECHNICAL FIELD

This invention relates generally to a joint, a laminate, and a method of preparing the surface of an alloy member for bonding to another layer of metal and, in particular, to a joint, a laminate, and a method of preparing the surface of a nickel-titanium alloy member for bonding to another layer of metal and, electively, to similar or dissimilar members.

BACKGROUND OF THE INVENTION

A problem in bonding to nickel-titanium alloys such as Nitinol is that as the alloy is heated, desirable properties such as shape memory or superelasticity are commonly destroyed or severely degraded as the alloy is heated through its annealing temperature range. The loss of these desirable properties is also a function of the size and shape of the alloy member, as well as the time period and temperature of the applied heat. In medical applications, nickel-titanium alloy wires are commonly used to form baskets, filters, and the like that are percutaneously introduced into the patient with an introducer catheter or sheath. When the nickel-titanium wire is welded or brazed, the shape memory or superelastic properties are typically destroyed or severely degraded. As a result, a short length of stainless steel cannula is typically crimped to attach a nickel-titanium wire to itself or another device component, which undesirably stiffens the overall device and contributes to its overall bulk.

As suggested, one prior art technique for bonding two or more metallic members together is welding, in which the members are heated to their melting points and deformed. The annealing temperature of nickel-titanium alloys such as Nitinol ranges from 350 degrees to 950 degrees Fahrenheit depending on the time period that a particular temperature is applied. Since the annealing temperature range is well below the typical 2350 degree Fahrenheit melting temperature of Nitinol, welding nickel-titanium alloy wires clearly destroys the desirable shape memory and superelastic properties of the alloy particularly at the weld joint.

Another prior art technique for bonding two or more metallic members is brazing, in which a bonding material is typically heated above 425 degrees Celsius (797 degrees Fahrenheit) but below the melting temperature of the metallic members. However, brazing normally exceeds the annealing temperatures of nickel-titanium alloys, and as a result, desirable shape memory and superelastic properties are, again, typically destroyed or severely degraded.

Another bonding technique that utilizes even lower temperatures is soldering. Soldering utilizes a solder material typically having a melting point below 425 degrees Celsius. The melting point of the solder material is a function of the proportional weights of the constituent metals. Although melting temperatures of solder materials are somewhat lower, soldering may also destroy or severely degrade desirable characteristic properties of the nickel-titanium alloy member if the activation temperature of the soldering flux and the melting temperature of the solder material are too high.

Another problem with soldering to nickel-titanium alloys such as Nitinol is that these alloys readily form an outer layer of titanium oxide which prevents fluxes from wetting and solder material from flowing on the surface to form a good metallic bond or joint. The oxidation also contaminates and weakens the joint. One solution to the oxidation layer problem is the addition of one or more layers of an interface material for adhering both to the nickel-titanium alloy member surface and the bonding material. Several techniques for depositing these interface layers include electroplating or applying compounds, solutions, powders, or fluxes to the nickel-titanium alloy member surface. However, many of these techniques also present the same previously described heat problem. Another problem with adding these interface layers is that the plated surface may not have the same desirable characteristic properties as the nickel-titanium alloy member. In the case of nitinol, a nickel-plated surface exhibits local loss of flexibility and increased tendency to crack or flake when the member is flexed.

Prior to applying a material or adding interface layers to the surface of a nickel-titanium alloy member, contaminants such as titanium oxide must be removed. One solution for removing contaminants is the application of a cleaning fluid or flux. Here again, the flux must have an activation temperature lower than a particular annealing temperature of the nickel-titanium alloy for preventing destruction and degradation of desirable characteristic properties. Traditional fluxes that remove the titanium oxide from the surface of nickel-titanium alloys have activation temperatures typically above the nominal annealing temperature of the alloy. Again, the use of these fluxes destroys or severely degrades the superelasticity or shape memory properties of the alloy as the nominal annealing temperature is approached. Other mechanical solutions for removing contamination are sanding, grinding, scraping, or applying an abrasive paste to the surface of the alloy. Ultrasonic cleaning is also available to shake oxidation particles free from the alloy surface. Physically removing oxidation, however, typically leaves a residue to contaminate the metallic bond.

Still another problem with nickel-titanium alloys is that a clean surface oxidizes rapidly, even within fractions of a second when exposed to air. To prevent recurrent oxidation and contamination, gas atmosphere reduction may be utilized in which a nonoxidizing or inert gas is provided during the bonding process. Of course, the contaminants must also be removed in a nonoxidizing environment. A disadvantage of this technique is the use of an evacuation or vacuum chamber.

SUMMARY OF THE INVENTION

The foregoing problems are solved and a technical advance is achieved in an illustrative joint, laminate, and method for preparing the surface of a nickel-titanium alloy member for bonding a layer of another metal thereto. The method comprises applying to the surface of the nickel-titanium alloy member a flux having an activation temperature below a predetermined annealing temperature of the alloy member. The activated flux has a composition of ingredients suitable for removing the contaminant from the surface and for further removing at least portions of the titanium from the surface while leaving the nickel therein. The method also includes removing the flux with the contaminant and at least portions of titanium suspended therein from the member surface while leaving nickel therein to form a nickel-rich interface surface for bonding to another metal layer such as solder material. As a result, a low temperature solder material is advantageously flowed on the nickel-rich interface surface to form a good metallic bond without affecting the shape memory or superelastic properties of the nickel-titanium alloy. In distinction to the multi-step technique of adding interface layers to the alloy surface, this method advantageously provides for the ready removal of problematic contamination as well as leaching titanium from the alloy member surface. The coating flux with the contaminant and titanium suspended therein also advantageously minimizes further oxidation of the nickel-rich interface surface.

Removing or scrubbing the contaminant from the alloy member surface includes heating the flux to its activation temperature and suspending the contaminant in the flux. The step of removing also includes at least partially leaching titanium from the member alloy surface with the flux heated to its activation temperature. The method further includes cooling the flux to form a solid coating of the flux on the nickel-rich interface surface after the flux-heating step. To advantageously strengthen the metallic bond, the flux is scrubbed from the alloy member surface to remove the suspended contaminant and titanium from the nickel-rich interface surface. Additional flux is applied to the scrubbed nickel-rich interface surface to leach additional titanium and to remove any remaining contaminants or oxidation.

The method further comprises flowing the other metal such as a tin-silver solder material to the nickel-rich interface surface and displacing from the interface surface the coating of flux with the contaminant and titanium suspended therein. Any remaining residual flux is then cleaned from the alloy member surface after the application of the solder material thereto.

The method of soldering a nickel-titanium alloy member includes the basic surface preparation method steps in addition to applying a molten solder having a melting point below a predetermined annealing temperature of the alloy member to the nickel-rich interface surface, positioning another metal member in contact with the molten solder, and cooling the molten solder to join the alloy member to the other metal member.

The soldering method includes the use of a nickel-titanium alloy having nickel by weight in a range of 50 to 58 percent and titanium by weight in a range of 50 to 42 percent. The flux utilized in the soldering method comprises an aluminum flux paste having at least one of tin chloride, zinc chloride, hydrofluoric acid, and ethanolamine as active ingredients. The nickel-rich interface surface in the soldering method has titanium by weight in a range of approximately 49.5 to 0 percent and nickel by weight in a range of 50.5 to 100 percent. The solders utilized in the soldering method are selected from the group of gold, nickel, indium, tin, silver, cadmium, lead, zirconium, and hafnium. The second member in the soldering method is a nickel-titanium alloy wire which has a surface prepared in the same manner as the nickel-rich interface surface of the alloy member. Alternatively, the second member in the soldering method is a wire or wire coil selected from the group consisting of stainless steel and platinum.

To further enhance the strength of the metallic bond between the nickel titanium alloy member and the other metal, the method further comprises at least partially removing titanium oxide from the surface of the nickel-titanium alloy before applying the flux thereto. In particular, the soldering method includes applying a pickling solution to at least partially remove the contaminant from the surface of the alloy member prior to applying the flux.

The joint comprises a nickel-titanium alloy member, an interface surface formed in the surface of the alloy member, a bonding material flowed on and adhering to the interface surface, and another member adhering to the bonding material. The interface surface has a contaminant removed therefrom and a predetermined amount of titanium at least partially removed therefrom with the flux heated to its activation temperature. The joint further comprises a bonding material comprising a soft solder having a melting temperature below 425 degrees Celsius. One such bonding material comprises a silver solder. The other member of the joint also has an interface surface adhering to the bonding material.

The joint is also characterized as including a base substrate of a metal alloy having by weight a first predetermined percentage of nickel and a second predetermined percentage of titanium, superelastic and shape memory properties, and an annealing temperature above which these superelastic and shape memory properties are impaired. The joint also comprises an interface surface on the base substrate and having by weight a third percentage of nickel greater than the first percentage and a fourth percentage of titanium less than the second percentage, and a solder material having a melting temperature less than the annealing temperature of the base metal alloy adhering to the interface surface. The joint further comprises a second member having an outside surface bonded to the solder material. The interface layer of this joint is formed by wetting a surface of the metal alloy with the flux having an activation temperature below a predetermined annealing temperature of the metal alloy and removing with the flux a contaminant on the interface surface and at least partially removing titanium from the interface surface.

The joint is formed by coating the interface layer with the flux having suspended therein the contaminant and the titanium at least partially removed from the alloy surface, flowing the solder material on the interface layer, and displacing the solder material flowing on the interface layer with the flux having the contaminant and titanium suspended therein. The joint is further formed by cleaning the flux from the base substrate and the solder material.

The laminate comprises a base member of a nickel-titanium alloy, an upper surface of the base member having a lower percentage of titanium than throughout the base member as a whole, a layer of solder material bonded to the upper surface and a second member bonded to the solder material layer. The base member has titanium by weight in a range of 50 to 42 percent and nickel by weight in a range of 50 to 58 percent. The range of titanium to nickel in the upper surface is by weight in a range of 49.5 to 0 percent and 50.5 to 100 percent. The solder material of the laminate is selected from the group consisting of gold, nickel, indium, tin, silver, cadmium, lead, zirconium, and hafnium. The second member of the laminate is selected from the group consisting of nickel-titanium alloys, stainless steel, and platinum.

DETAILED DESCRIPTION

Depicted in FIGS. 1-8 is an illustrative preferred method of preparing the surface of a nickel-titanium alloy member wire for bonding thereto a layer of another metal, such as a solder material, and, electively, thereto another similar or dissimilar member. The method further includes soldering the nickel-titanium alloy member wire to the other member and forming a solder joint therebetween. Also illustrated in FIGS. 1-8 is a joint comprising the nickel-titanium alloy member wire and an interface surface formed in the surface of the member wire with a flux heated to its activation temperature. The flux removes the titanium oxide contaminant layer from the surface and also leaches titanium from the surface to form a nickel-rich surface on which a solder material is readily flowed. The joint further includes a layer of solder or other bonding material flowed on the interface surface and a second member adhering to the solder material. Further illustrated in FIGS. 1-8 is a laminate comprising a base member of a nickel-titanium alloy with an upper surface of the base member having a lower percentage of titanium than throughout the base member as a whole, a layer of solder material bonded to the upper surface, and a second member bonded to the solder material layer.

Figure 1:
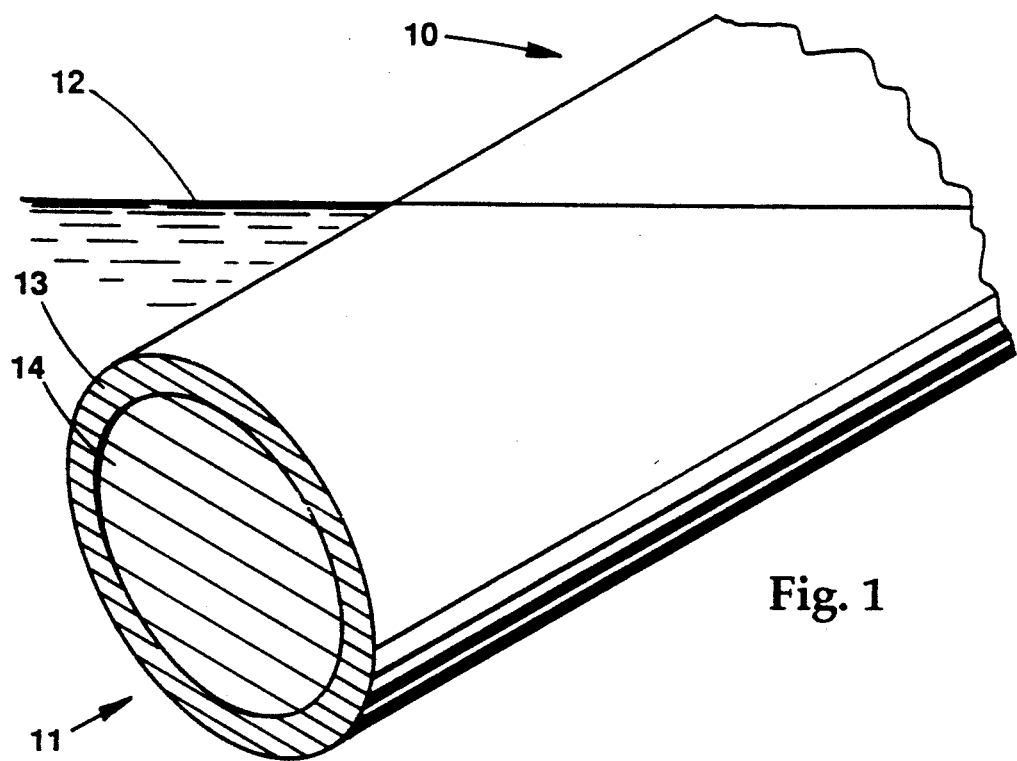
FIG. 1 depicts a partially sectioned view of a nickel-titanium alloy member wire placed in a pickling solution for at least partially removing a contaminant oxidation layer from the surface thereof to initiate the method of the present invention.

Depicted in FIG. 1 is a cross-sectional view of distal end 11 of nickel-titanium member alloy wire 10 submerged in pickling solution 12. The preferred method of preparing the surface of the nickel-titanium alloy member wire comprises the initial step of at least partially removing titanium oxide layer 13 from base metal substrate layer 14 of nickel-titanium alloy member wire 10. By way of example, pickling solution 12 comprises a mixture of 120 ml 52 percent concentration hydrofluoric acid, 600 ml 70 percent concentration nitric acid, and 4,000 ml water. The titanium oxide layer constitutes a contaminant that should at least be partially removed from the surface of the alloy member wire to assist the subsequently applied flux in the removal of the titanium oxide contaminant from the base metal layer. Depending on the depth of the titanium oxide layer, the member remains in the pickling solution preferably for a period of time such as between one to one and a half minutes to partially etch or dissolve the contaminant layer from the base metal alloy wire. Completion of this initial step is evidenced when the member wire with a polished, shiny surface changes color to a light grey or when the member wire with a blackened oxidation layer changes color to a dark grey. Experiments with a 0.024" nickel-titanium alloy member wire indicated that no better joint was formed even after the wire was submerged in the pickling solution for 30 minutes. In fact, leaving the wire in the pickling solution longer than one and a half minutes etched or dissolved the base metal.

Nickel-titanium alloy member wire 10 comprises a nickel-titanium alloy having nickel by weight in a range of 50 to 58 percent and titanium by weight in a range of 50 to 42 percent, respectively. Theoretically, when the nickel-titanium alloy contains these percentages of nickel and titanium, the alloy exhibits desirable well-known shape memory and superelastic characteristic properties. Practically, these desirable properties are more pronounceably exhibited with alloys including nickel by weight in a range of 52 to 57 percent and titanium by weight in a range of 48 to 43 percent, respectively. Iron by weight of up to 3 percent is added in particular applications to add strength to the alloy. In such a case, the alloy contains 52 percent nickel, 45 percent titanium, and 3 percent iron. Trace elements of under 100 ppm per element of chromium, copper, iron, molybdenum, zinc, zirconium, and hafnium are permitted. Up to 1 percent of chromium and iron are also permitted in the alloy; however, normally no more than 0.2 percent of chromium and iron are added to the alloy to alter the well-known transformation temperature between the martensite and austenite states of the alloy. The transformation temperature of the alloy may also be changed 10 to 12 degrees Celsius by the drawing process utilized for the nickel-titanium alloy member wire. Nickel-titanium alloy wire, such as Nitinol, is commercially available from Shape Memory Applications, Inc., Sunnyvale, Calif., and others.

Figure 2:
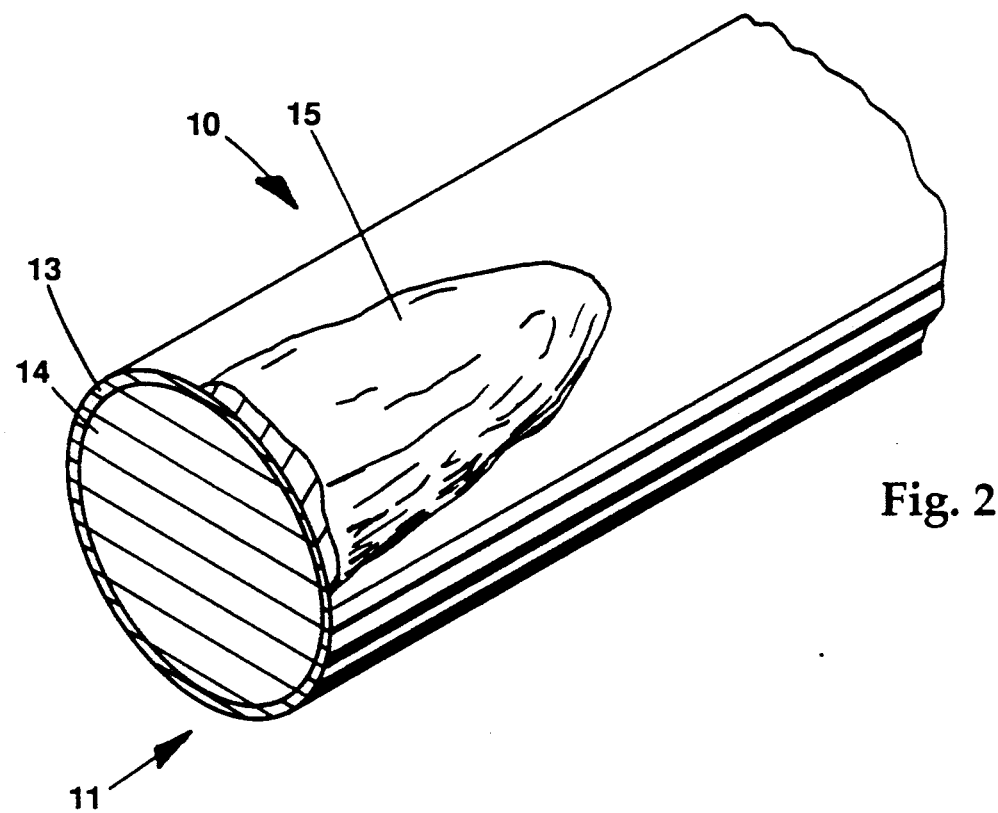
FIG. 2 depicts the nickel-titanium alloy member wire of FIG. 1 with the contaminant oxidation layer partially removed and a flux applied thereto.

Depicted in FIG. 2 is alloy member wire 10 of FIG. 1 removed from the pickling solution. Titanium oxide contaminant layer 13 has been reduced in thickness by the pickling solution, and flux 15 is applied over a portion of the reduced thickness oxidation layer. Similar to aluminum oxide with respect to aluminum, titanium oxide readily forms on the surface of the nickel-titanium metal wire. Reoxidation of the alloy member wire occurs within fractions of a second after the pickling solution has removed the oxide layer and base metal 14 has been exposed to air. The flux, commonly known as Indalloy Flux No. 3, is an aluminum flux paste commercially available from Indium Corporation of America, Utica, N.Y. The active ingredients of the flux and their concentration by weight percentage include tin chloride ($SnCl_2$) 13.0 percent, zinc chloride ($ZnCl_2$) 8.0 percent, concentrated hydrofluoric acid (HF-48% active) 14.0 percent, and ethanolamine ($HOCH_2CH_2NH_2$) 65.0 percent. Recommended mixing of these ingredients includes dissolving the tin chloride and zinc chloride in the hydrofluoric acid and then adding the ethanolamine. Since the hydrofluoric acid is a very active ingredient, the tin chloride and zinc chloride should be completely dissolved in the hydrofluoric acid prior to adding the ethanolamine. The ethanolamine should be added very slowly to the hydrofluoric acid solution to prevent a violent reaction, which can be further avoided by monitoring the temperature of the acid solution for large and rapid increases. Protective wear and a ventilated hood should also be utilized.

Figure 3:
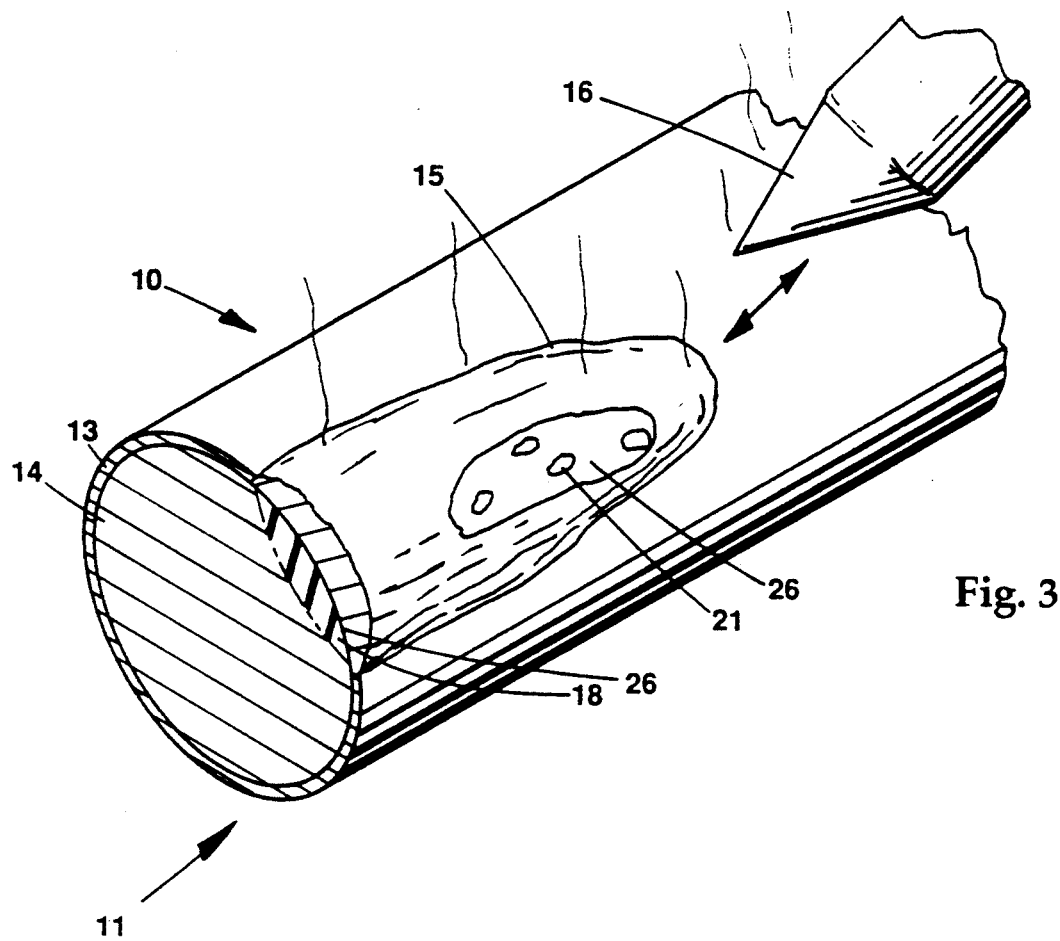
FIG. 3 depicts the alloy member wire of FIG. 2 with the flux heated to its activation temperature for removing the contaminant oxidation layer thereunder and at least partially leaching titanium from the surface of the base metal to form a nickel-rich interface surface.

FIG. 3 depicts alloy member wire 10 of FIG. 2 with flux 15 being heated to its activation temperature. The activation temperature of this preferred flux is approximately 200 degrees Fahrenheit, and is heated thereto using, for example, soldering iron 16 set to approximately 450 degrees Fahrenheit. The soldering iron temperature is set at the lower end of the 350 to 950 degree Fahrenheit range of annealing temperatures of the alloy member wire. Since the heat of the soldering iron is only being applied for a short time to heat the flux to its activation temperature and to flow subsequently applied solder material, the 450 degree Fahrenheit temperature does not adversely effect the shape memory and superelastic properties of alloy member wire 10. The activation temperature of this flux may also range as high as 650 degrees Fahrenheit, which is still below the nominal 750 degree Fahrenheit annealing temperature of nickel-titanium member wire 10. However, the preferred activation temperature of the flux is maintained as low as possible so as not to adversely effect the shape memory and superelastic properties of the wire. Heat activated flux 15 removes reduced thickness titanium oxide layer 13 thereunder and suspends the oxidation therein. The activated flux also removes or leaches titanium from the surface of the base metal nickel-titanium alloy wire layer to form a nickel-rich interface surface 26. The activated flux also leaches titanium from the base metal layer to form a nickel-rich layer 18 under interface surface 26. The leached titanium is believed to combine with the chlorides of the flux to form titanium tetrachloride (TiCl4) which is suspended in the flux. The activated flux with the removed titanium oxide contaminant and leached titanium suspended therein coats the nickel-rich interface surface 26 and layer 18 to prevent further oxidation or reoxidation of the surface or layer. When the soldering iron is removed, the activated flux cools, forming a solidified coating.

Also shown in FIG. 3 is a top partially cut-away view of nickel-rich interface surface 26 under the activated flux with islands 21 of titanium oxide remaining thereon. This is due to the unevenness or to the nonuniformity of the titanium oxide layer, the flux layer, and the base metal alloy surface. The nickel-rich surface includes titanium by weight in a range of approximately 49.5 to 0 percent and nickel by weight in the range of 50.5 to 100 percent, depending on the initial concentration of the alloy member wire. The nickel-rich surface and layer includes a higher percentage of nickel and a lower percentage of titanium than that of base metal alloy layer 14. A higher percentage of nickel or a lower percentage of titanium increases the flow of solder material on the interface surface and strengthens the metallic bond therebetween. The preferred method also includes wiping or scrubbing the activated flux with the removed titanium oxide particles and leached titanium suspended therein from nickel-rich interface surface 26. This is performed by wiping the flux from the surface of the wire in a well-known manner or scrubbing the surface by submerging and agitating the surface of the wire in a soapy water solution. Not all of the flux is removed in this process. However, the remaining coating of flux acts to prevent further oxidation or reoxidation of the surface.

Figure 4:
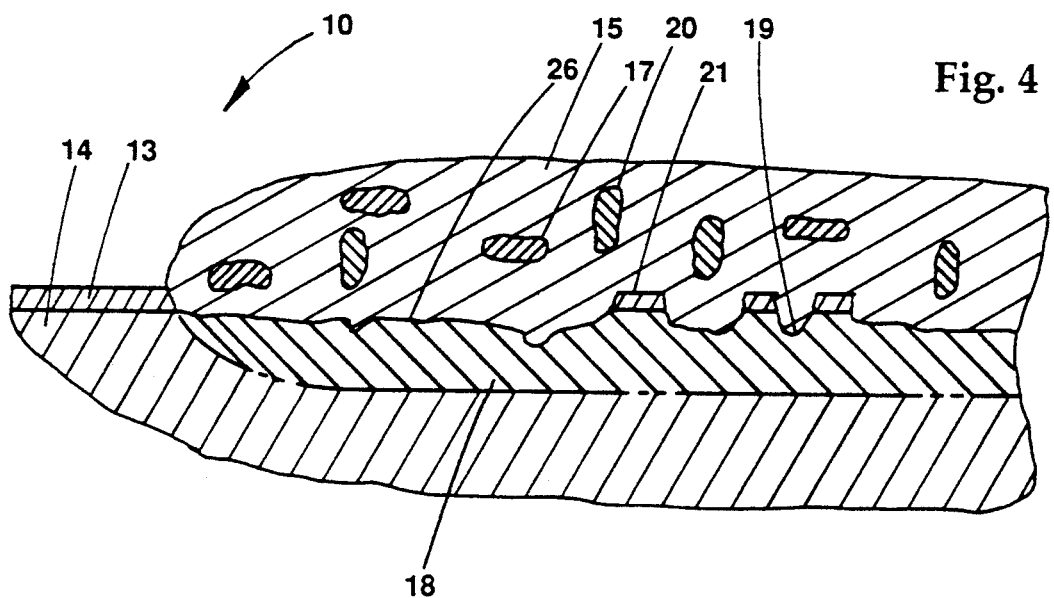
FIG. 4 depicts an enlarged sectional view of the alloy member wire of FIG. 3 illustrating the base metal, nickel-rich interface surface and layer, and the activated flux with the removed contaminant and the leached titanium suspended therein.

FIG. 4 depicts an enlarged, longitudinal sectional view of FIG. 3 illustrating base metal layer 14 of alloy wire 10, nickel-rich interface surface 26, nickel-rich interface layer 18, and flux 15 thereon with removed titanium oxide particles 17 from titanium oxide layer 13 suspended therein. The activated flux also leaches titanium from the base metal alloy member surface shown as particles 20 and suspends them therein as titanium tetrachloride. As shown, nickel-rich interface surface 26 is etched having pores 19 formed therein with residual islands 21 of titanium oxide remaining thereon. Titanium is at least partially removed or etched from the surface of the alloy member wire, leaving nickel-rich interface surface 26 and layer 18.

Figure 5:
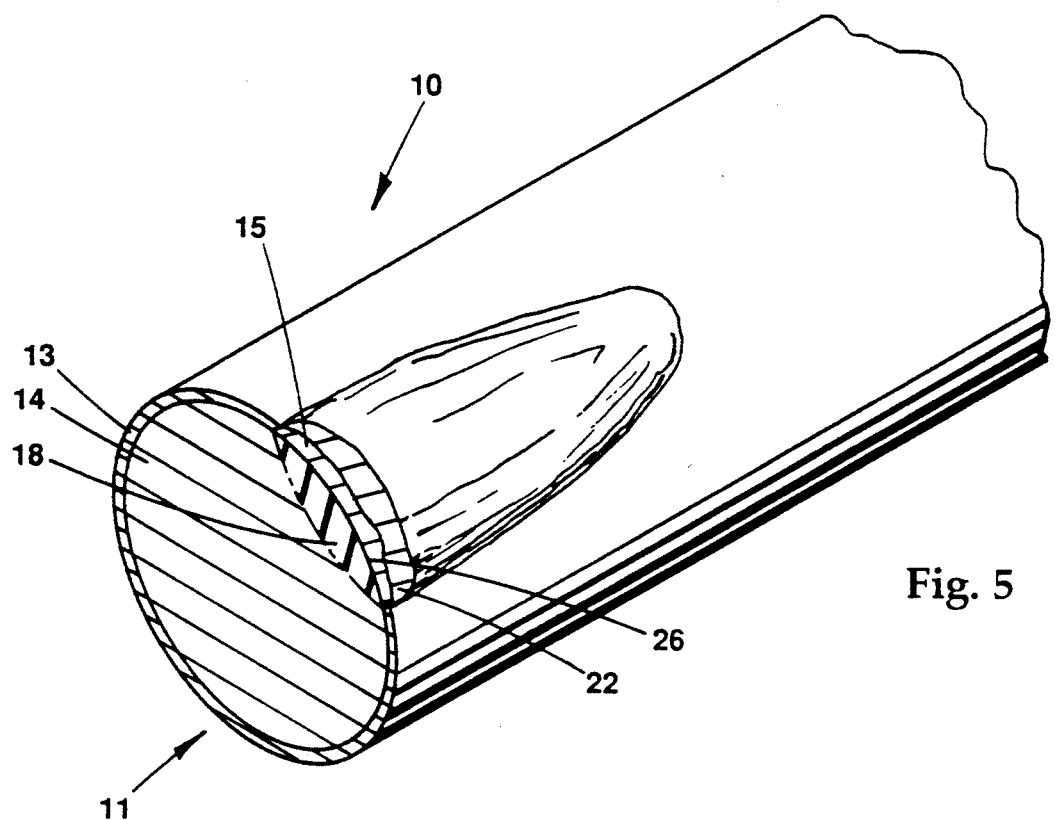
FIG. 5 depicts the alloy member wire of FIG. 3 with the initial flux layer scrubbed and an additional layer of flux applied thereover for removing any remaining contaminant on and leaching additional titanium from the nickel-rich interface surface thereof.

FIG. 5 depicts alloy member wire 10 of FIG. 3 with initial flux layer 15 partially scrubbed from the surface of the wire and an additional layer of flux 22 applied thereover. The additional layer of flux when activated removes and suspends any titanium oxide remaining on the surface thereof and further leaches and suspends titanium from interface surface 26 and interface layer 18 of alloy member wire 10. Although this step is not absolutely necessary, experiments have indicated that the solder joint or laminate formed by base metal layer 14, nickel-rich surface 26, and a solder material is 25 percent stronger. Likewise, the step of submerging or applying a pickling solution to the titanium oxide layer also increases the strength of the solder joint or laminate by another 25 percent.

Additional flux layer 22 is heated to its activation temperature to suspend any additional titanium oxide contaminant particles and to further leach titanium from the nickel-rich interface surface and layer. Additional flux layer 22 also provides a liquid or solidified coating to protect the nickel-rich interface surface and layer of the wire from further oxidation or reoxidation.

Figure 6:
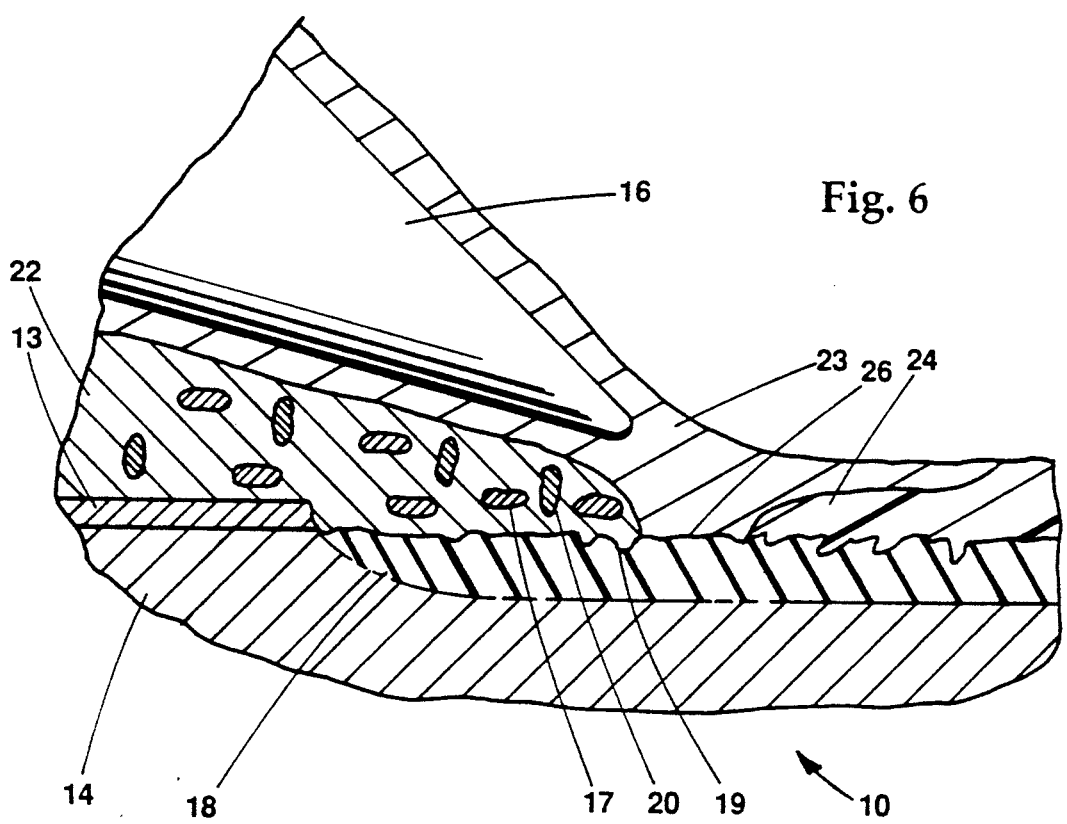
FIG. 6 depicts an enlarged partially sectioned view of the alloy member wire of FIG. 5 with molten solder material flowing onto the nickel-rich interface surface and displacing the coating flux layer.

Depicted in FIG. 6 is an enlarged, partially sectioned, longitudinal view of alloy member wire 10 of FIG. 5 with molten solder material 23 being flowed on nickel-rich interface surface 26 and displacing flux coating 22 therefrom. Soldering iron 16 heats flux 22 having removed titanium oxide particles 17 and leached titanium particles 20 suspended therein to above its activation temperature and solder material 23 to a molten state. Molten solder material 23 flows on nickel-rich interface surface 26 and then cools to form solidified solder material 24 and a good metallic bond with nickel-rich interface surface 26 and layer 18. The flowing molten solder material fills pores 19 in and on nickel-rich interface surface 26 and layer 18. As molten solder material 23 flows on the nickel-rich interface surface, flux coating 22 is burned off or displaced onto titanium oxide layer 13. As a result, a joint is formed comprising base metal nickel-titanium alloy 14, interface layer 18 and surface 26 having a percentage of nickel greater than the base metal alloy, and solder material 24. This joint can also be characterized or described as a laminate comprising a base member of a nickel-titanium alloy 14 and upper surface 26 of the base member having a lower percentage of titanium than throughout the base member as a whole, and a layer of solder material 24 bonded to upper surface 26. As previously described, solder material 24 adheres to nickel-rich interface surface 26 and has a melting point temperature less than the annealing temperature of the base metal alloy so as not to adversely effect the shape memory and superelastic properties of the base metal alloy member wire.

The preferred solder material for the joint or laminate is a tin-silver composition consisting by weight of 96.5 percent tin and 3.5 percent silver and having a melting temperature of 221 degrees Celsius (429 degrees Fahrenheit). The metallic bond formed by this composition solder is qualitatively described as excellent. The solder material may also be formed from the group of elements consisting of gold, nickel, indium, tin, silver, cadmium, lead, zirconium, and hafnium. Table A includes a list of commercially available solders along with their compositions and melting point temperatures as well as a qualitative assessment of the resulting metallic bond formed with a 0.024" nitinol alloy member wire. This table includes only solder material tested, and other comparable solder material formed from the above group of elements and their equivalents are contemplated.

TABLE A

| Indium Company No. | Composition (By Weight Percent) | Melting Point (°C.) | Results |
|---|---|---|---|
| 150 | 81 Pb, 19 In | 280 | fair |
| 201 | 91 Sn, 9 Zn | 199 | fair |
| 9 | 70 Sn, 18 Pb, 12 In | 162 | poor |
| 104 | 62.5 Sn, 36.1 Pb, 1.4 Ag | 179 | fair |
| 8 | 44 In, 42 Sn, 14 Cd | 93 | good |
| 1 | 50 In, 50 Sn | 125 | poor |
| 133 | 95 Sn, 5 Sb | 240 | good |
| 2 | 80 In, 15 Pb, 5 Ag | 155 | fair |
| 204 | 70 In, 30 Pb | 174 | good |
| 106 | 63 Sn, 37 Pb | 183 | fair |
| 10 | 75 Pb, 25 In | 260 | good |
| 7 | 50 In, 50 Pb | 269 | poor |
| 181 | 51.2 Sn, 30.6 Pb, 18.2 Cd | 145 | good |
| 165 | 97.5 Pb, 1.5 Ag, 1 Sn | 309 | good |
| 164 | 92.5 Pb, 5 In, 2.5 Ag | 310 | good |
| 171 | 95 Pb, 5 In | 314 | good |
| 121 | 96.5 Sn, 3.5 Ag | 221 | excellent |
| Allstate Company | 96 Sn, 4 Ag | 220 | excellent |
| Western Gold & Platinum Company | 80 Au, 20 Sn | 280 | poor |

To measure the advantages of the pickling solution step and the step of applying an additional layer of flux, pull-tests were performed on a 0.024" diameter nitinol wire tapered to 0.004" with a 0.004" platinum wire coil wound around the tapered end. Joint breakage occurred with 2 to 3 pounds applied for a single flux layer joint, 3 to 5 pounds applied for a double flux layer joint, and 4.5 to 7 pounds applied to a double flux layer and pickling solution prepared joint. The 0.004" diameter nitinol wire tip usually broke with 7 pounds applied thereto. In addition, pull-tests were performed on a 0.024" diameter Nitinol wire bonded with a 3 mm by 2 mm tin-silver solder joint to a wire of platinum, stainless steel, and nitinol. Table B includes a summary of the results obtained from these pull-tests.

TABLE B

| Metal | Pull Test Results in Pounds | | | | |
|---|---|---|---|---|---|
| | Test 1 | Test 2 | Test 3 | Test 4 | Test 5 |
| Platinum | 6.5 | 5.5 | 6.2 | 6.2 | 6.5 |
| Stainless Steel | 4.3 | 4.2 | 5.0 | 4.2 | 4.2 |
| Nitinol | 4.0 | 3.5 | 3.7 | 3.5 | 3.8 |

The pull-tests indicated that the platinum wire formed the strongest joint with the 0.024" Nitinol wire. Since platinum is highly solderable, this result was expected. Stainless steel is extremely difficult to solder, thus the lower strength pull-test result was also expected. The Nitinol to nitinol solder joint produced the lowest strength pull-test results. The metallic bonding or soldering of Nitinol to Nitinol provides a joint in which the interface layer broke away from the base metal substrate even though wetting and flowing occurred. The solder material also appeared to fracture as the interface layer broke away from the base metal substrate. Nevertheless, the Nitinol to Nitinol joint still provided a satisfactory bond for use in medical devices such as wire guides and the like. It is also contemplated that the use of a separate flux formulated for each different material for removing contaminants such as oxidation from the surface thereof would form a stronger joint. For example, the use of a flux specifically designed for wetting stainless steel and a separate flux for wetting the Nitinol wire would be contemplated to provide a stronger joint when the two metals were soldered together.

Figure 7:
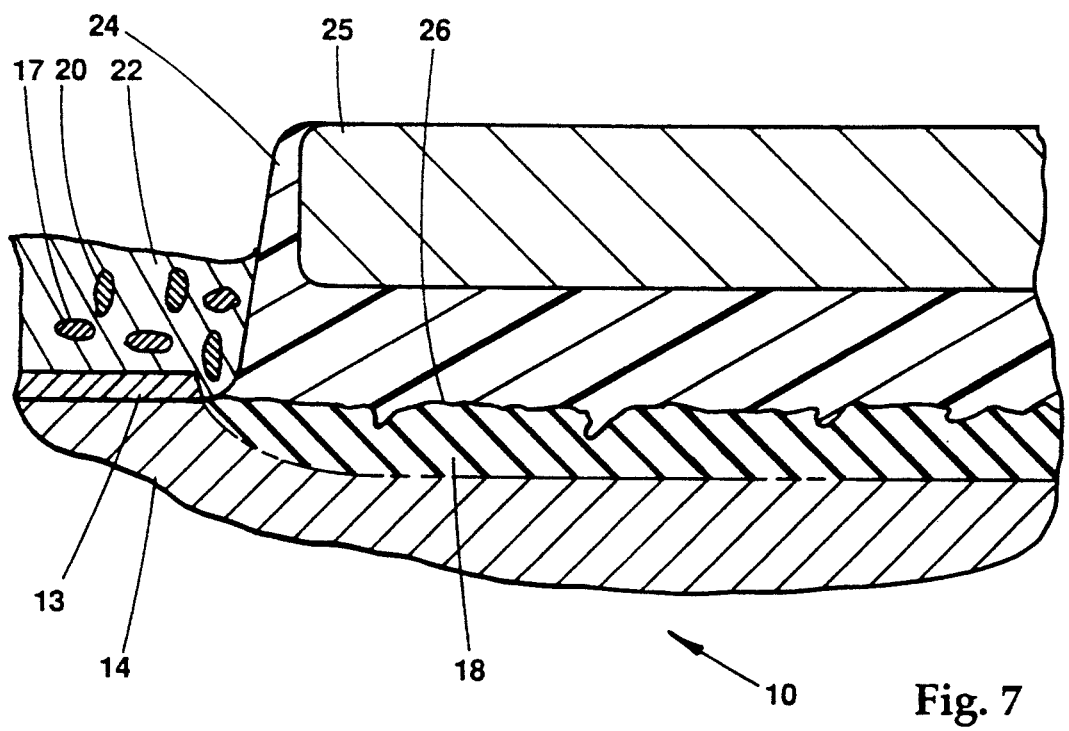
FIG. 7 depicts the alloy member wire of FIG. 6 with another member being applied to the molten solder and cooling the solder on the nickel-rich surface and the other member to form a laminate or joint therebetween.

Depicted in FIG. 7 is alloy member 10 of FIG. 6 with another metallic member 25 having been added to the molten solder and cooled to form solidified material 24. As a result, metallic member 25 is bonded or adheres to the solder material to form a laminate or joint. Metallic member 25 may be another nickel-titanium member wire having a nickel-rich interface surface formed therein, a stainless steel alloy member, a platinum member, or other metal member. Member 25 is applied to the molten solder which cools to form solidified solder material 24 for bonding two members together. The molten solder flows on nickel-rich interface surface 26 of layer 18 and the surface of member 25. The molten solder material is cooled to bond the two members together. Thus, a joint is formed comprising a nickel-titanium alloy member 10, an interface layer 18 formed in the surface of the member and having titanium oxide contaminant 13 removed and a predetermined amount of titanium at least partially removed therefrom with flux 22 heated to its activation temperature. The joint further comprises a bonding material 24 coated on and adhering to interface layer 18 and member 25 bonded to the same solder material 24. The joint may also be characterized as a base substrate 14 of a metal alloy having by weight a given percentage of nickel and titanium resulting in an alloy having superelastic and shape memory properties. The metal alloy has an annealing temperature above which the superelastic and shape memory properties are impaired. The joint further comprises nickel-rich interface layer 18 on base substrate 14 which has a greater percentage of nickel and a lower percentage of titanium than of the base substrate. Solder material 24 has a melting temperature less than the annealing temperature of the base metal alloy adhering to interface layer 18. The joint is formed as previously described. As previously suggested, flux 22 with removed titanium oxide contaminant particles 17 and titanium 20 suspended therein is displaced by the molten solder onto titanium oxide layer 13. Flux 22 also forms a layer over solidified solder material 24 as shown.

Figure 8:
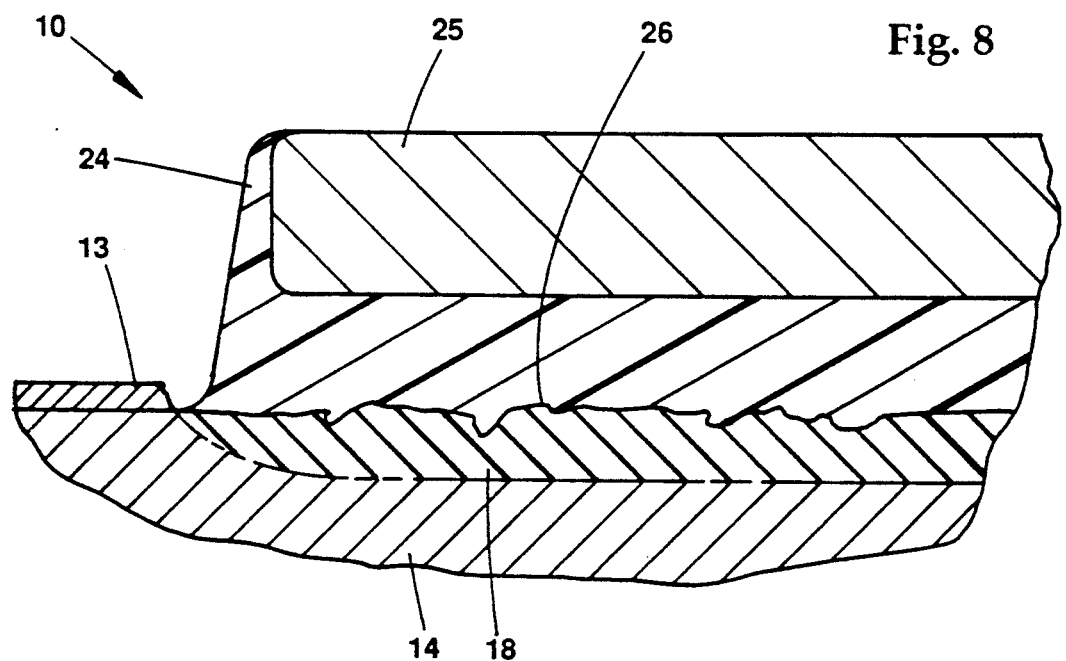
FIG. 8 depicts the joint or laminate of FIG. 7 with the flux scrubbed from the surfaces of the alloy member wire and the other member.

Depicted in FIG. 8 is a sectioned view of the solder joint of FIG. 7 and further illustrating the step of scrubbing the flux from the surfaces of alloy member wire 10 and other member 25. The flux is cleaned from the titanium oxide layer 13 as well as the solidified solder material 24 using any of a number of well-known techniques, for example, the use of water with mechanical scrubbing or the use of ultrasound, abrasives, or cleaning solutions.

A number of experiments were performed using the joint laminate, and method for preparing the surface of a Nitinol wire and bonding to a layer of metal such as solder material and, electively, to another member. One test was conducted to determine whether the flux removed titanium as well as titanium oxide from the wire surface. The outside diameter of the Nitinol wire was measured, and the wire was treated with flux at the activation temperature for several hours. The outside diameter of the wire exhibited a significant decrease past the depth of the oxidation, indicating that material was removed from the surface of the base metal nickel-titanium alloy member wire. After treatment, the surface of the Nitinol wire resisted oxidation in air, indicating that titanium was removed from the nickel-rich surface of the Nitinol wire which remained for bonding solder material thereto.

One specific example of the use of the method with respect to a percutaneous medical device known as a wire guide was utilized in soldering a 0.004" platinum wire coil having an outside diameter of 0.014" and a length of 2 to 3 cm to a 0.024" diameter Nitinol mandril wire approximately 165 to 180 cm in length. The distal end of the Nitinol mandril wire was tapered to 0.004" and the platinum wire coil positioned over the tapered distal end. The Nitinol mandril wire was submerged in the aforementioned pickling solution for one and a half minutes, and a first layer of Indalloy aluminum flux paste No. 3 was applied to distal 1.5 to 2 cm about the tapered distal end of the wire. The flux was heated to above its activation temperature of 200 degrees Fahrenheit with a 430 degree Fahrenheit soldering iron tip. The activated flux was wiped from the distal end of the tapered mandril wire. The platinum wire coil was placed over the tapered distal end of the mandril wire, and an additional layer of flux paste applied to the wire coil and mandril. The additional layer of flux was then heated to above its activation temperature and Indium tin-silver solder No. 121 was flowed on the wetted distal end. The solder readily flowed over the wire coil and tapered distal end of the mandril wire. The solder was allowed to cool, thereby forming a metallic bond or joint between the platinum wire coil and the Nitinol mandril wire. Other medical devices using a nickel-titanium or nitinol alloy member are contemplated.

In summary, the present invention solves the problem of bonding or soldering to nickel-titanium alloys such as Nitinol and without adversely degrading the desirable shape memory and superelastic properties of the alloy. The flux utilized with this invention advantageously removes the outer layer of titanium dioxide from the surface of the alloy, which heretofore had prevented traditional fluxes from wetting and solder material from flowing on the surface to form a good metallic bond or joint. The results from the use of this flux was totally unexpected since the flux was designated for use with aluminum. Furthermore, Indalloy Flux No. 2, which is a specialty flux mixture for soldering high chromium content alloys, was suggested for use in soldering to Nitinol, but did not even flow tin-silver solder No. 121. The flux of the present invention advantageously removes the titanium oxide contaminant layer from the surface of the nitinol and further provides a coating layer to prevent reoxidation of the base metal substrate during the soldering process. Heretofore, nickel-titanium alloys such as Nitinol were believed not solderable. Unexpectedly, the present invention solves these problems by providing an acceptable joint by which Nitinol is bondable to itself and other metals and, in addition, without affecting the shape memory and superelastic properties of the nitinol. Previously, it was known that Nitinol could be brazed; however, the brazing process destroyed the shape memory and superelastic properties of the alloy, which renders it unacceptable for many medical device applications.

The solder joint, laminate, and the method of preparing the surface of the nickel-titanium alloy member for bonding solder material thereto have been illustrated and described in the drawing and foregoing description, the same is to be considered illustrative and not restrictive in character. It is to be understood that only the preferred embodiment has been shown and that all changes and modifications that come within the scope of the claims are to be protected. In particular, it is contemplated that different composition solder materials may be utilized that more closely conform to the desired characteristics, such as flexibility, tensile strength, and hardness of the nickel-titanium alloy member. Furthermore, the percentages of nickel and titanium in the alloy may be varied or other small percentages of elements utilized to exhibit modified or different shape memory and superelastic properties and to provide different annealing temperatures. Additionally, any flux of any composition having an activation temperature below the annealing temperature of the alloy and having similar or equivalent component elements to remove titanium from the base metal alloy are also contemplated. It is further contemplated that a high temperature solder material may be used to form a small initial joint, and a larger deposit of a low temperature solder material be subsequently applied to form a stronger overall joint. This is particularly useful when bonding materials that are extremely difficult to solder such as when soldering wires end to end or soldering Nitinol to Nitinol. The method of preparing a nickel-titanium alloy member surface for bonding another layer of metal thereto is believed to involve the removal of the outside titanium oxide layer and the leaching of titanium from the base metal substrate. However, the use of the aluminum paste flux is not completely understood since the use of this flux with aluminum involves removing the outside aluminum oxide layer and replacing aluminum in the base metal substrate with zinc which is present in the flux. Accordingly, it is contemplated that titanium in the base metal substrate of the alloy may be replaced with zinc in the flux. However, since the results of the present invention were totally unexpected, only further tests can substantiate or refute this contemplation.

What is claimed is:

1. A method of preparing a surface of a nickel-titanium alloy member having an annealing temperature above which selected properties are impaired and a contaminant on the surface thereof for bonding a layer of an other metal thereto, the method comprising the steps of:

applying to said member surface a flux having an activation temperature below said annealing temperature of said alloy member, said flux having a composition suitable for removing said contaminant from said member surface and for further removing at least portions of titanium from said member surface while leaving nickel therein; and removing with said flux said contaminant and at least portions of titanium from said member surface while leaving nickel therein to form a nickel-rich interface surface for bonding said other metal layer thereto.

2. The method of claim 1 wherein said step of removing said contaminant from said member surface includes heating said flux to said activation temperature and suspending said contaminant in said flux.

3. The method of claim 2 wherein said step of removing at least portions of said titanium includes at least partially leaching titanium from said member surface with said flux heated to said activation temperature.

4. The method of claim 2 and further comprising the step of cooling the flux to solidify said flux and form a solid coating of said flux on said nickel-rich interface surface after said flux-heating step.

5. The method of claim 1 wherein said removing step comprises heating said flux to said activation temperature and scrubbing from said member surface said flux having therein said contaminant and titanium removed from said nickel-rich interface surface.

6. The method of claim 5 further comprising applying additional flux to said scrubbed nickel-rich interface surface.

7. The method of claim 6 further comprising flowing said other metal in a molten state on said nickel-rich interface surface after applying said additional flux.

8. The method of claim 5 further comprising flowing said other metal in a molten state on said nickel-rich interface surface.

9. The method of claim 1 further comprising applying said other metal in a molten state to said nickel-rich interface surface and displacing from said nickel-rich interface surface of said flux with said contaminant and said titanium removed from said nickel-rich interface surface.

10. The method of claim 9 further comprising cleaning said flux from said alloy member after applying said other metal thereto.

11. The method of claim 1 further comprising applying a pickling solution to at least partially remove said contaminant from said member surface prior to applying said flux to said member surface.

12. A method of soldering a nickel-titanium alloy member having selected properties comprising the steps of:
preparing a surface of said alloy member according to claim 1;
applying a molten solder having a melting point below said annealing temperature of said alloy member to said nickel-rich interface surface thereof;
positioning a second metal member in contact with said molten solder; and
cooling said molten solder to join said alloy member to said second member.

13. The method of claim 12 wherein said nickel-titanium alloy member has nickel by weight in a range of 50 to 58 percent and titanium by weight in a range of 50 to 42 percent.

14. The method of claim 12 wherein said flux comprises an aluminum flux paste having at least one of tin chloride, zinc chloride, hydrofluoric acid, and ethanolamine as active ingredients.

15. The method of claim 12 wherein said nickel-rich interface surface has titanium by weight in a range of approximately 49.5 to 0 percent and nickel by weight in a range of 50.5 to 100 percent.

16. The method of claim 12 wherein said solder is selected from the group consisting of gold, nickel, indium, tin, silver, cadmium, lead, zirconium, and hafnium.

17. The method of claim 12 wherein said second member is a nickel-titanium alloy wire which has a surface prepared in the same manner as said nickel-rich interface surface of said alloy member.

18. The method of claim 12 wherein said second member is a wire coil selected from the group consisting of stainless steel and platinum.

19. The method of claim 12 further comprising removing oxide from said surface of said nickel-titanium alloy member before the flux-applying step.

20. Method of soldering an alloy member including nickel and titanium and having oxidation thereon to an other member, comprising the steps of:
applying a pickling solution to at least partially remove said oxidation from a surface of said alloy member;
wetting said surface with a flux of at least one of chlorides and fluorides having an activation temperature below an annealing temperature of said alloy, said annealing temperature representing that temperature above which certain properties of said alloy member are impaired;
heating said flux to said activation temperature;
suspending said contaminant in said flux heated to said activation temperature;
leaching at least partially said titanium from said surface to form a nickel-rich interface surface with said flux heated to said activation temperature;
suspending said titanium at least partially leached from said surface in said flux heated to said activation temperature;
coating said nickel-rich interface surface with said flux having said contaminant and said titanium suspended therein;
scrubbing from said nickel-rich interface surface said flux having said contaminant and said titanium suspended therein;
wetting said nickel-rich interface surface with an additional amount of said flux;
flowing a silver solder in a molten state on said nickel-rich interface surface and said other member;
displacing from said nickel-rich interface surface said additional flux with said solder flowing on said nickel-rich interface surface;
cooling said solder on said nickel-rich interface surface and said other member; and
cleaning said flux from said alloy member and said other member.

21. A joint comprising:
a nickel-titanium alloy member;
an interface surface formed in a surface of said alloy member, being substantially contaminant free, and having titanium at least partially removed therefrom with a flux heated to its activation temperature;
a bonding material flowed on and adhering to said interface surface; and
a second member adhering to said bonding material.

22. The joint of claim 21 wherein said bonding material comprises a soft solder having a melting temperature below 425 degrees Celsius.

23. The joint of claim 21 wherein said bonding material comprises a silver solder.

24. The joint of claim 21 further comprising said second member having an interface surface adhering to said bonding material.

25. A joint comprising:
a base structure of a metal alloy having by weight a first percentage of nickel and a second percentage of titanium, superelastic and shape memory properties, and an annealing temperature above which said superelastic and shape memory properties are impaired;
an interface surface on said base substrate and having by weight a third percentage of nickel greater than said first percentage and a fourth percentage of titanium less than second percentage; and
a solder material having a melting temperature less than said annealing temperature of said metal alloy adhering to said interface surface.

26. The joint of claim 25 further comprising a second member having an outside surface bonded to said solder.

27. The joint of claim 25 wherein said interface layer is formed by:
wetting a surface of said metal alloy with a flux having an activation temperature below said annealing temperature of said alloy; and
removing with said flux a contaminant on said interface surface and at least partially said titanium from said interface surface.

28. The joint of claim 27 formed by:
coating said interface surface with said flux having suspended therein said contaminant and said titanium at least partially removed from said member surface;
flowing said solder material on said interface surface; and
displacing with said solder material flowing on said interface surface said flux having said contaminant and said titanium suspended therein.

29. The joint of claim 28 further formed by cleaning said flux from said base substrate, said interface surface, and said solder material.

30. A laminate comprising:
a base member of a nickel-titanium alloy having superelastic properties;
an upper surface of said base member having a lower percentage of titanium than throughout the base member as a whole;
a layer of solder material bonded to the upper surface; and
a second member bonded to the solder layer;
wherein the bond between the base member and said second member is at least 3.5 pounds.

31. A laminate according to claim 30 wherein the base member has titanium by weight in a range of 50 to 42 percent and nickel by weight in a range of 50 to 58 percent.

32. A laminate according to claim 31 wherein a range of titanium to nickel in the upper surface is by weight in a range of 49.5 to 0 percent to 50.5 to 100 percent.

33. A laminate according to claim 30 wherein the solder material is selected from the group consisting of gold, nickel, indium, tin, silver, cadmium, lead, zirconium, and hafnium.

34. A laminate according to claim 30 wherein the second member is selected from the group consisting of nickel-titanium alloys, stainless steel, and platinum.

35. An article having a solder joint made in accordance with the method of claim 12.

36. An article having a solder joint made in accordance with the method of claim 20.

37. A method of preparing a surface of a nickel-titanium alloy member having an annealing temperature above which selected properties are impaired and a contaminant on the surface thereof for bonding an other metal member thereto, the method comprising the steps of:
applying to said member surface an aluminum flux paste having an activation temperature below said annealing temperature of said alloy member, said flux having a composition suitable for removing said contaminant from said surface member;
removing with said flux said contaminant from said member surface to form a substantially contaminant-free bonding surface on said alloy member;
flowing a solder material in a molten state on said bonding surface and thereby displacing said flux from said bonding surface; and
cooling said solder material to a solid state.

38. The method of claim 37 wherein the step of removing said contaminant from said member surface includes heating said flux to said activation temperature and suspending said contaminant in said flux.

39. The method of claim 37 wherein the temperature of the molten solder is below the annealing temperature of the alloy member.

40. The method of claim 39 wherein the solder is selected from the group consisting of gold, nickel, indium, tin, silver, cadmium, lead, zirconium and hafnium.

41. The method of claim 37 wherein the aluminum flux paste has at least one of tin chloride, zinc chloride, an inorganic acid and ethanol amine and equivalents thereof as an active ingredient.

42. A method of soldering an alloy member including nickel and titanium and having oxidation thereon to an other member, said alloy member having at least one of superelastic and shape memory properties and an annealing temperature above which said superelastic and shape memory properties are impaired, said method comprising the steps of:
applying a pickling solution to at least partially remove said oxidation from a surface of said alloy member;
wetting said surface with an aluminum flux paste having an activation temperature below said annealing temperature of said alloy;
heating said flux to said activation temperature;
suspending said contaminant in said flux heated to said activation temperature;
scrubbing from said surface said flux having said contaminant suspended therein;
wetting said surface with an additional amount of said aluminum paste flux;
flowing the solder in a molten state on said surface and on said other member to thereby displace from said surface said additional flux with said solder flowing on said surface;
cooling said solder on said surface and on said other member; and
cleaning said flux from said alloy member and said other member.

43. The method of claim 42 wherein said aluminum flux paste has at least one of tin chloride, zinc chloride, hydrofluoric acid, ethanolamine, and equivalents thereof, as active ingredients.

44. A method of flowing a solder material on a surface of a nickel-titanium alloy member having $TiO_2$ on the surface thereof and an annealing temperature above which superelastic and shape memory properties are impaired, comprising the steps of:
- applying to said member surface an inorganic acid based flux having an activation temperature below said annealing temperature of said alloy member, said flux having a composition suitable for removing said $TiO_2$ from said member surface;
- removing with said flux said $TiO_2$ from said member surface to form a bonding surface substantially free of said $TiO_2$;
- flowing a solder material in a molten state on said bonding surface; and
- cooling said solder material to a solid state.

45. The method of claim 44 further comprising providing said flux with at least one of tin chloride, zinc chloride, nickel chloride, hydrofluoric acid, ethanolamine, and equivalents thereof.

46. A method of flowing a solder material on a surface of a nickel-titanium alloy member having $TiO_2$ on the surface thereof and an annealing temperature above which superelastic and shape memory properties are impaired, comprising the steps of:
- applying to said member surface an aluminum flux paste having an activation temperature below said annealing temperature of said alloy member, said flux having a composition suitable for removing said $TiO_2$ from said member surface;
- removing with said flux said $TiO_2$ from said member surface to form a bonding surface substantially free of said $TiO_2$;
- flowing a solder material in a molten state on said bonding surface; and
- cooling said solder material to a solid state.

* * * * *